US012593821B2

(12) United States Patent
Wernimont et al.

(10) Patent No.: US 12,593,821 B2
(45) **Date of Patent: *Apr. 7, 2026**

(54) SYSTEMS AND METHODS FOR DETERMINING DATA RELATING TO AN ANIMAL USING A RECHARGEABLE DEVICE

(71) Applicant: Hill's Pet Nutrition, Inc., Topeka, KS (US)

(72) Inventors: Susan Wernimont, Lawrence, KS (US); Jodi Vondran, Wamego, KS (US); Robin Thompson, Northumberland (GB)

(73) Assignee: Hill's Pet Nutrition, Inc., Overland Park, KS (US)

( * ) Notice: Subject to any disclaimer, the term of this patent is extended or adjusted under 35 U.S.C. 154(b) by 248 days.

This patent is subject to a terminal disclaimer.

(21) Appl. No.: 17/982,954

(22) Filed: Nov. 8, 2022

(65) Prior Publication Data

US 2023/0145392 A1 May 11, 2023

Related U.S. Application Data

(60) Provisional application No. 63/278,293, filed on Nov. 11, 2021, provisional application No. 63/278,250, (Continued)

(51) Int. Cl.
*A01K 11/00* (2006.01)
*A01K 27/00* (2006.01)
(Continued)

(52) U.S. Cl.
CPC .......... *A01K 11/006* (2013.01); *A01K 11/008* (2013.01); *A01K 27/009* (2013.01); (Continued)

(58) Field of Classification Search
CPC .. A01K 11/006; A01K 11/008; A01K 27/009; A01K 29/005; A61B 5/0022; (Continued)

(56) References Cited

U.S. PATENT DOCUMENTS

| | | |
|---|---|---|
| 7,231,254 B2 | 6/2007 | DiLorenzo |
| 7,263,953 B2 | 9/2007 | Sundararajan |

(Continued)

FOREIGN PATENT DOCUMENTS

| | | |
|---|---|---|
| AU | 2003101051 | 2/2004 |
| CN | 104871997 | 9/2015 |

(Continued)

OTHER PUBLICATIONS

Belk, Russell W., "Metaphoric Relationships with Pets", The White Horse Press Cambridge UK, 1996, pp. 121-145 (25 pages).

(Continued)

*Primary Examiner* — Omeed Alizada

(57) ABSTRACT

Described herein are systems and methods for tracking an animal comprising—for example: an electronic device configured to be coupled to an animal, the electronic device comprising: one or more sensors comprising at least one of an accelerometer, a gyroscope, or a magnetometer, the one or more sensors configured to determine location or movement information relating to the animal; a memory device configured to store the location or movement information relating to the animal; a communication interface configured to wirelessly communicate the location or movement information to an external device; and a battery device for providing power the at least one of the one or more sensors or the communication interface; and a charging device configured to wirelessly provide power to the battery device.

16 Claims, 7 Drawing Sheets

Related U.S. Application Data filed on Nov. 11, 2021, provisional application No. 63/278,240, filed on Nov. 11, 2021.

(51) Int. Cl.

| | |
|---|---|
| *A01K 29/00* | (2006.01) |
| *A61B 5/00* | (2006.01) |
| *H02J 50/00* | (2016.01) |
| *H04W 4/80* | (2018.01) |

(52) U.S. Cl.

CPC .......... *A01K 29/005* (2013.01); *A61B 5/0022* (2013.01); *A61B 5/0031* (2013.01); *H02J 50/00* (2016.02); *H04W 4/80* (2018.02); *A61B 2503/40* (2013.01); *A61B 2562/0219* (2013.01); *A61B 2562/0223* (2013.01)

(58) Field of Classification Search

CPC .............. A61B 5/0031; A61B 2503/40; A61B 2562/0219; A61B 2562/0223; H02J 50/00; H04W 4/80

See application file for complete search history.

(56) References Cited

U.S. PATENT DOCUMENTS

| | | | |
|---|---|---|---|
| 7,434,541 | B2 | 10/2008 | Kates |
| 7,616,124 | B2 | 11/2009 | Paessel et al. |
| 7,633,397 | B2 | 12/2009 | Dugan |
| 7,914,468 | B2 | 3/2011 | Shalon et al. |
| 8,305,220 | B2 | 11/2012 | Gibson |
| 9,220,444 | B2 | 12/2015 | Russell |
| 9,226,692 | B2 | 1/2016 | Haas |
| 9,420,766 | B2 | 8/2016 | Triener |
| 9,572,647 | B2 | 2/2017 | Couse et al. |
| 9,717,216 | B1 | 8/2017 | Schlachta et al. |
| 9,788,232 | B2 | 10/2017 | Goldfain |
| 9,823,138 | B2 | 11/2017 | Zakharov et al. |
| 9,872,481 | B2 | 1/2018 | Goldfain |
| 10,091,972 | B1 | 10/2018 | Jensen et al. |
| 10,149,617 | B2 | 12/2018 | Couse |
| 10,154,655 | B2 | 12/2018 | Schab et al. |
| 10,194,639 | B2 | 2/2019 | Jordan |
| 10,314,292 | B2 | 6/2019 | Thorne |
| 10,463,023 | B2 | 11/2019 | Perz-Camargo et al. |
| 10,492,473 | B2 | 12/2019 | Menkes et al. |
| 10,716,492 | B2 | 7/2020 | Filipowicz |
| 11,229,361 | B2 | 1/2022 | Coen et al. |
| 11,582,948 | B2 | 2/2023 | Garrity et al. |
| 2002/0010390 | A1* | 1/2002 | Guice .................... G16H 50/20 |
| | | | 600/300 |
| 2005/0197546 | A1 | 9/2005 | Mardiks et al. |
| 2006/0150918 | A1 | 7/2006 | Rowe |
| 2008/0132922 | A1 | 6/2008 | Buevich et al. |
| 2009/0076346 | A1 | 3/2009 | James et al. |
| 2010/0191071 | A1 | 7/2010 | Anderson et al. |
| 2011/0125063 | A1 | 5/2011 | Shalon et al. |
| 2011/0169610 | A1* | 7/2011 | Geissler .................. H04Q 9/00 |
| | | | 340/10.1 |
| 2011/0181399 | A1 | 7/2011 | Pollack et al. |
| 2012/0053657 | A1 | 3/2012 | Parker et al. |
| 2012/0274442 | A1 | 11/2012 | Mottram |
| 2014/0136118 | A1 | 5/2014 | Zanghi et al. |
| 2014/0267299 | A1 | 9/2014 | Couse |
| 2014/0331942 | A1 | 11/2014 | Sarazyn |
| 2015/0119726 | A1 | 4/2015 | Matsuno et al. |
| 2015/0181840 | A1 | 7/2015 | Tupin, Jr. et al. |
| 2015/0379860 | A1 | 12/2015 | Vardi |
| 2016/0012748 | A1 | 1/2016 | Donavon |
| 2016/0042038 | A1 | 2/2016 | Schumacher et al. |
| 2016/0165853 | A1 | 6/2016 | Goldfain |
| 2016/0178392 | A1 | 6/2016 | Goldfain |
| 2016/0262356 | A1 | 9/2016 | Perez-Camargo et al. |
| 2016/0301218 | A1 | 10/2016 | Cho et al. |
| 2017/0050599 | A1 | 2/2017 | Gilbert et al. |
| 2017/0064926 | A1 | 3/2017 | Gutierrez |
| 2017/0095206 | A1 | 4/2017 | Leib et al. |
| 2017/0105389 | A1 | 4/2017 | Sanchez |
| 2017/0164843 | A1* | 6/2017 | Ehm .................... A61B 5/0205 |
| 2017/0196196 | A1 | 7/2017 | Trottier et al. |
| 2017/0231533 | A1 | 8/2017 | Qu et al. |
| 2018/0028095 | A1 | 2/2018 | Yamamoto |
| 2018/0084755 | A1 | 3/2018 | Hirsch |
| 2018/0132455 | A1 | 5/2018 | Pradeep et al. |
| 2018/0146645 | A1 | 5/2018 | Arbel |
| 2019/0069518 | A1 | 3/2019 | Falbaum |
| 2019/0110684 | A1* | 4/2019 | Coen ...................... G16H 40/67 |
| 2019/0133079 | A1 | 5/2019 | Jang |
| 2019/0183092 | A1 | 6/2019 | Couse et al. |
| 2019/0200577 | A1 | 7/2019 | Kath |
| 2019/0335714 | A1 | 11/2019 | Sweetnam et al. |
| 2020/0015452 | A1 | 1/2020 | Lund |
| 2020/0015740 | A1 | 1/2020 | Alnofeli |
| 2020/0060545 | A1 | 2/2020 | Maher et al. |
| 2020/0068853 | A1 | 3/2020 | Radovcic |
| 2020/0205381 | A1 | 7/2020 | Wernimont et al. |
| 2020/0236901 | A1 | 7/2020 | Trottier et al. |
| 2020/0253165 | A1 | 8/2020 | Luciew et al. |
| 2020/0335999 | A1 | 10/2020 | Pan et al. |
| 2020/0358316 | A1 | 11/2020 | Shirsat et al. |
| 2021/0065277 | A1 | 3/2021 | Bramson et al. |
| 2021/0256833 | A1 | 8/2021 | Daoura et al. |
| 2021/0298631 | A1 | 9/2021 | Varadarajan et al. |
| 2022/0087229 | A1 | 3/2022 | Wernimont et al. |
| 2022/0104464 | A1 | 4/2022 | Wernimont et al. |
| 2022/0151207 | A1 | 5/2022 | Mott et al. |
| 2022/0183559 | A1 | 6/2022 | Forsell |
| 2022/0339549 | A1 | 10/2022 | Johnson |
| 2022/0354092 | A1 | 11/2022 | Marin |
| 2023/0057275 | A1 | 2/2023 | Seo |
| 2023/0141529 | A1 | 5/2023 | Wernimont et al. |
| 2023/0145392 | A1 | 5/2023 | Wernimont et al. |
| 2023/0147909 | A1 | 5/2023 | Wernimont et al. |
| 2023/0369916 | A1 | 11/2023 | Kim et al. |

FOREIGN PATENT DOCUMENTS

| | | |
|---|---|---|
| CN | 112401888 | 2/2021 |
| EP | 3264299 | 1/2018 |
| EP | 3586618 | 1/2020 |
| GB | 2492110 | 12/2012 |
| JP | 4209294 | 1/2009 |
| JP | 2016521386 | 7/2016 |
| JP | 2017506876 | 3/2017 |
| JP | 2018174885 | 11/2018 |
| JP | 2018-198553 | 12/2018 |
| KR | 20210072643 | 6/2021 |
| KR | 20210123893 | 10/2021 |
| KR | 102422186 | 7/2022 |
| WO | 2015/069037 | 5/2015 |
| WO | 2016/029138 | 2/2016 |
| WO | 2016/061529 | 4/2016 |
| WO | 2016/185742 | 11/2016 |
| WO | 2019/175115 | 9/2019 |
| WO | 2019/178222 | 9/2019 |
| WO | 2020/139652 | 7/2020 |
| WO | 2022/066282 | 3/2022 |
| WO | 2022/072049 | 4/2022 |
| WO | 2023/086315 | 5/2023 |
| WO | 2024/025877 | 2/2024 |

OTHER PUBLICATIONS

Belshaw, et al., "Slower, shorter, sadder: a qualitative study exploring how dog walks change when the canine participant develops osteoarthritis",BMC Veterinary Research, 2020, pp. 1-8.

Bentopal,"Interactive Dog Toy Wicked Ball for Indoor Cats/Dogs with Motion Activated/USB Rechargeable",https://www.amazon.com/BENTOPAL-Interactive-Wicked-Activated-Rechargeable/dp/B0862BBL8V, Retrieved [online] Oct. 24, 2022,pp. 1-10.

Cheerble,"Wicked Ball",https://www.cheerble.com/products/wickedball?variant=31808965476470, Retrieved [online] Oct. 24, 2022,pp. 1-2.

(56) References Cited

OTHER PUBLICATIONS

Copol,"Cat Toy, Interactive Cat Toys for Indoor Cats, Automatic Cat Toy with Replace Feather/LED Light/ Bird Chirping,Electric USB Charging 360°Self Rotating Ball, Kitten Feather Toys(Pink)". https://www.amazon.com/Interactive-Automatic-Chirping%EF%BC%8CElectric-Charging-360%C2%B0Self/dp/B09BFDSXD3, Retrieved [online] Oct. 24, 2022,pp. 1-7.

Coy et al., "Why Can't I Resist Those "Puppy Dog" (or "Kitty Cat") Eyes? A Study of Owner Attachment and Factors Associated with Pet Obesity", https://www.mdpi.com/2076-2615/11/2/539, Feb. 19, 2021, pp. 1-12.

den Uijl, Ingrid, et al. "External validation of a collar-mounted triaxial accelerometer for second-by-second monitoring off eight behavioural states in dogs." PloS one 12.11 (Nov. 29, 2017): e0188481. https://journals.plos.org/plosone/article?id=10.1371/journal.pone.0188481, retrieved Sep. 23, 2020, pp. 1-9.

Dicola, T., "Cat Purr Detection FFT: Fun with Fourier Transforms", https://learn.adafruit.com/fft-fun-with-fourier-transforms/cat-purr-detection, Retrieved [online] Oct. 24, 2022, pp. 1-3.

DogcareHQ," Best Interactive Dog Toys: Entertainment and Development", Smart Dog Stuff, https://dogcarehq.com/bes-interactive-dog-toys/ retrieved [online] Oct. 24, 2022, pp. 1-33.

Fable,"The Game- Best Dog Enrichment Toy & Feeder in One", https://fablepets.com/products/the-game, Retrieved [online] Oct. 24, 2022,pp. 1-11.

FitBark 2 Dog Activity Monitor | Health & Fitness Tracker for Dogs | Waterproof, Small & Leightweight (10 g) | Not a GPS Tracker, Amazon.com, https://www.amazon.com/FitBark-Dog-Activity-Monitor-Black/dp/B077MDJYKQ, retrieved Oct. 1, 2020, pp. 1-10.

Griffies, et al., "Wearable sensor shown to specifically quantify pruritic behaviors in dogs", BMC Veterinary Research, Apr. 3, 2018, pp. 1-10.

Hansen, B. D. et al., Evaluation of an accelerometer for at-home monitoring of spontaneous activity in dogs, (Jun. 2007) American Journal of Veterinary Research, vol. 68(5), pp. 468-475 (8 pages), ResearchGate, https://www.researchgate.net/publication/6358541_Evaluation_of_an_accelerometer for at-home_monitoring_of_spontaneous_activity_in_dogs, retrieved Oct. 1, 2020.

Hielm-Bjorkman, et al., "Psychometric testing of the Helsinki chronic pain index by completion of a questionnaire in Finnish by owners of dogs with chronic signs of pain caused by osteoarthritis", American Journal of Veterinary Research vol. 70 No. 6, Jun. 2009, pp. 727-734 (8 pages).

International Search Report and the Written Opinion of the International Searching Authority issued in International Application PCT/US2021/043833 mailed Oct. 28, 2021, pp. 1-11.

International Search Report and the Written Opinion of the International Searching Authority issued in International Application PCT/US2021/043879 mailed Nov. 9, 2021, pp. 1-10.

Ladha C., et al., Gaitkeeper: A System for Measuring Canine Gait, Sensors (Basel, Switzerland) provided by Multidisciplinary Digital Publishing Institute (MDPI), Feb. 8, 2017, 17(2):309, pp. 1-23.

Ladha, C., et al. "A step in the right direction: an open-design pedometer algorithm for dogs." BMC veterinary research 14.1 (Mar. 20, 2018): 107. https://bmcvetres.biomedcentral.com/articles/10.1186/s12917-018-1422-3, retrieved Sep. 20, 2020, pp. 1-17.

Link AKC Smart Dog Collar with GPS Tracker & Activity Monitor (Leather or Sport), Amazon.com, https://www.amazon.com/LINK-AKC-Smart-Dog-Collar/dp/B01MFG7ELX, retrieved Oct. 1, 2020, pp. 1-9.

Petgeek, "Interactive Dog Toys, Durable Motion Activated Automatic Dog Bone for Medium & Large Dogs Boredom, Electronic Dog Enrichment Toys to Chase, USB Rechargeable", https://www.amazon.com/PETGEEK-Electronic-Interactive-Automatic-Material/dp/B08B5SP3GP, Retrieved [online] Oct. 24, 2022,pp. 1-11.

PetPace Smart Collar with 12 Months Pet Plus Monitoring, Amazon.com, https://www.amazon.com/PetPace-Smart-Collar-Medium/dp/B01N1A2WKL, retrieved Oct. 1, 2020, pp. 1-7.

Sefon,"Robotic Cat Toys Interactive, 1000 mAh Large Capacity Battery Operated with USB Charging, Auto/RC 3 Mode Timed with 4 Feathers/Birds/Mouse Toys for Indoor Cats, All Floors Carpet Available",https://www.amazon.com/YicoGomo-Smart-Interactive-Toys-Entertainment/dp/B089YT6KG9/ref=cm_cr_arp_d_product_top?ie=UTF8,Retrieved [online] Oct. 24, 2022,pp. 1-7.

Singleton, S., CONTROL4—Home Automation Blog, "How to choose the right home security system",https://www.control4.com/blog/399/how-to-choose-the-right-home-security-system/, Mar. 17, 2017,pp. 1-7.

Skymee, "Owl Robot: Movable Full HD Pet Camera with Treat Dispenser, Interactive Toy for Dogs and Cats, Mobile Control via App", https://www.amazon.com/SKYMEE-Owl-Robot-Dispenser-Interactive/dp/B07YCCYMH4, Retrieved [online] Oct. 24, 2022, pp. 1-11.

Trixie, "Activity Flip Board Activity Strategy Game Dog Toy". https://www.chewy.com/trixie-activity-flip-board-activity/dp/134668, Retrieved [online] Oct. 24, 2022, pp. 1-7.

Tsai, et al., "Generating consumer terminology to describe emotions in pet owners and their pets", Center for Sensory Analysis and Consumer Behavior, Jun. 21, 2020, pp. 1-13.

Vaataja, et al., "Happy Dogs and Happy Owners Using Dog Activity Monitoring Technology in Everyday Life", University of Tampere, Dec. 4, 2018, pp. 1-12.

Vetsens—Activityscope: https://vetsens.co.uk/products/activityscope/, retrieved Sep. 23, 2020, pp. 1-4.

Webb, et al., "What is animal happiness?", New York Academy of Sciences, 2019, pp. 62-76 (15 pages).

Wernimont, et al., "Use of Accelerometer Activity Monitors to Detect Changes in Pruritic Behaviors: Interim Clinical Data on 6 Dogs", www.mdpi.com/journal/sensors, Jan. 16, 2018, pp. 1-12.

Whistle 3 GPS Pet Tracker Activity Monitor Grey: Pet Supplies, Whistle Go & Go Explore-The Ultimate Health + Location Tracker for Pets, Amazon.com, https://www.amazon.com/Whistle-GPS-Track-Activity-Monitor/dp/B01N7MWKWY, retrieved Oct. 1, 2020, pp. 1-7.

White G.A. et al., ""Who's been a good dog?"—Owner perceptions and motivations for treat giving", ScienceDirect, Sep. 15, 2016, p. 14-19.

Wickedbone, "Smart Bone, Automatic & Interactive Toy for Dog, Puppy and Cat, App Control, Safe & Durable, Keep Your Pets Entertained All Day", Amazon, (Oct. 7, 2018), Retrived Oct. 24, 2022, pp. 1-11.

Wiseman-Orr, et al., "Development of a questionnaire to measure the effects of chronic pain on health-related quality of life in dogs", American Journal of Veterinary Research vol. 65 No. 8. Aug. 2004, pp. 1077-1084 (8 pages).

Wiseman-Orr, et al., "Validation of a structured questionnaire as an instrument to measure chronic pain in dogs on the basis of effects on health-related quality of life", American Journal of Veterinary Research vol. 67 No. 11, Oct. 16, 2006, pp. 1826-1836 (11 pages).

Wrigglesworth, David J., et al. "Accuracy of the use of triaxial accelerometry to measuring daily activity as a predictor of daily maintenance energy requirement in healthy adult Labrador Retrievers" Abstract, https://avmajournals.avma.org/doi/abs/10.2460/ajvr.72.9.1151, Sep. 2011, vol. 72, No. 9,retrived Sep. 23, 2020, pp. 1-2.

WWVVPET," Interactive Cat Toys Ball with LED Light & Catnip, Upgraded Ring Bell Feather Pet Toy, Auto Spinning Smart Cat Ball Toy, USB Rechargeable Stimulate Hunting Instinct Kitty Funny Chaser Roller", https://www.amazon.com/Interactive-Spinning-Rotating-Intelligent-Rechargeable/dp/B08B16V3FN, (Jan. 5, 2021), Retrieved Oct. 24, 2022, pp. 1-9.

Zamkah, et al., "Identification of Suitable Biomarkers for Stress and Emotion Detection for Future Personal Affective Wearable Sensors", https://www.mdpi.com/2079-6374/10/4/40, Apr. 16, 2020, pp. 1-15.

International Search Report and the Written Opinion of the International Searching Authority issued in International Application PCT/US2022/049209 mailed May 15, 2023.

Partial international search report in PCT/US2022/049209 mailed Mar. 14, 2023.

International Search Report and the Written Opinion of the International Searching Authority issued in International Application PCT/US2023/028570 mailed Nov. 10, 2023.

WSPA, 2017, Identification Methods for Dogs & Cats, pp. 1-32.

(56) References Cited

OTHER PUBLICATIONS

How Do EID Tags Work? with wayback retrieval from Jul. 31, 2021
(Year:2021).

* cited by examiner

200

220 — Communication Interface

218 — Magnetometer

202 — Accelerometer

204 — Temperature Sensor

206 — Gyroscope

208 — Glucose Sensor

210 — Processor

212 — Memory

214 — GPS

216 — Battery

700

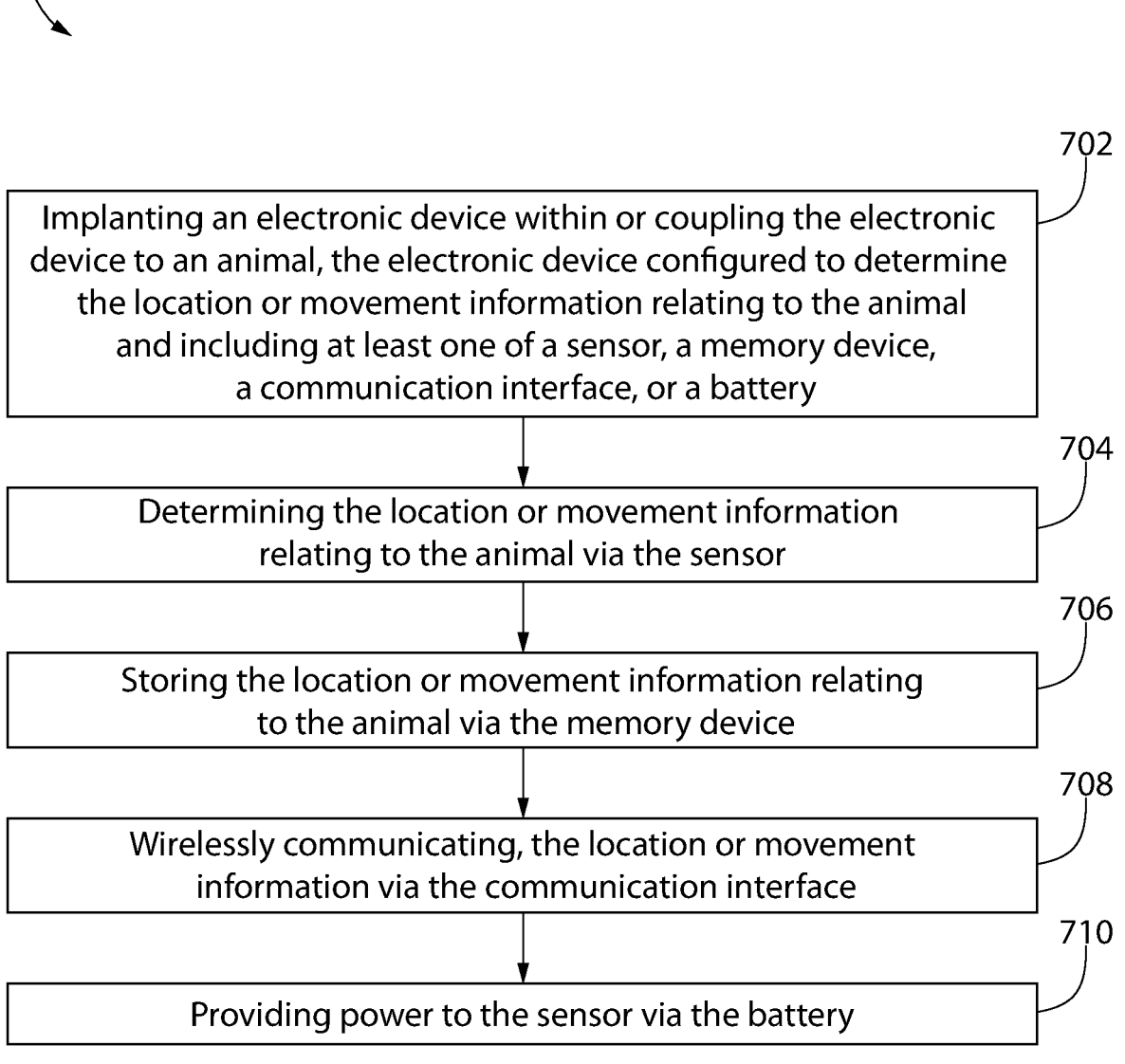

702

Implanting an electronic device within or coupling the electronic device to an animal, the electronic device configured to determine the location or movement information relating to the animal and including at least one of a sensor, a memory device, a communication interface, or a battery

704

Determining the location or movement information relating to the animal via the sensor

706

Storing the location or movement information relating to the animal via the memory device

708

Wirelessly communicating, the location or movement information via the communication interface

710

Providing power to the sensor via the battery

FIG. 7

SYSTEMS AND METHODS FOR DETERMINING DATA RELATING TO AN ANIMAL USING A RECHARGEABLE DEVICE

CROSS-REFERENCE TO RELATED APPLICATIONS

This application claims the benefit of priority from U.S. Provisional Application Nos. 63/278,240; 63/278,250; and 63/278,293, filed Nov. 11, 2021; the contents of which are hereby incorporated herein by reference in their entireties.

BACKGROUND

Movement or location data relating to an animal (e.g., a pet) can have many uses in understanding animal health, well-being, and behavior. Collars are known that can collect some behavior data of the animal. However, many animals do not wear collars, or they have a limited ability to wear collars. For example, animals may not wear collars due to the animal's size, due to the collar being uncomfortable for the animal, or due to owners of the animal preferring the animal to not wear a collar. Further, there may be safety concerns around collar use, especially if there is a danger of the collar getting caught on something and thereby presenting a choking hazard. Despite the reasons for an animal to not wear a collar, data relating to the animal is important to collect. Thus, it is desired that a device capable of monitoring behavioral data of an animal be implantable within the animal. Such device would be capable of monitoring the movement or location data of the animal without the animal wearing a collar, which would overcome the shortcomings described above.

BRIEF SUMMARY

The present disclosure may be directed, in an aspect, to a device, method, and/or system for determining location or movement information relating to the animal via an electronic device implanted within the animal. The electronic device may include at least one component comprising: one or more sensors comprising at least one of an accelerometer, gyroscope, or magnetometer, the one or more sensors configured to determine the location or movement information relating to the animal; a memory device configured to store the location or movement information relating to the animal; a communication interface configured to wirelessly communicate the location or movement information with an external device; and a battery device for providing power to the at least one of the accelerometer, gyroscope, or magnetometer. A charging device may be provided to wirelessly provide power to the electronic device.

In an aspect, the electronic device and the charging device may be implanted within the animal, although in other examples the electronic device may be implanted within the animal and the charging device may be located outside the animal. In an aspect, the charging device may be positioned within a food dish of the animal, bedding of the animal, or a waste area of the animal.

In an aspect, the electronic device may be housed within at least one of a contact lens, an earring, a tag, or a tooth crown worn by the animal. In an aspect, the electronic device may receive location or movement information from the external device at substantially the same time as the battery receives power from charging device. In an aspect, the charging device may provide power to the battery device via Bluetooth.

In some embodiments, the present invention provides a system for tracking an animal comprising: an electronic device configured to be coupled to an animal, the electronic device comprising: one or more sensors comprising at least one of an accelerometer, a gyroscope, or a magnetometer, the one or more sensors configured to determine location or movement information relating to the animal; a memory device configured to store the location or movement information relating to the animal; a communication interface configured to wirelessly communicate the location or movement information to an external device; and a battery device for providing power the at least one of the one or more sensors or the communication interface; and a charging device configured to wirelessly provide power to the battery device.

In other embodiments, the present invention provides a method for tracking an animal comprising: coupling an electronic device to an animal, the electronic device comprising: one or more sensors comprising at least one of an accelerometer, a gyroscope, or a magnetometer; a memory device operably coupled to the one or more sensors; a communication interface operably coupled to the memory device or the one or more sensors; and a battery device for providing power to at least one of the one or more sensors or the communication interface; and wirelessly providing power, via a charging device, to the battery device; determining, using the one or more sensors, location or movement information relating to the animal; storing, by the memory device, the location or movement information; and wirelessly communicating, by the communication interface, the location or movement information to an external device.

BRIEF DESCRIPTION OF THE DRAWINGS

The present disclosure will become more fully understood from the detailed description and the accompanying drawings, wherein:

FIG. 7 is an example process describing an implantable device providing information relating to an animal, as described herein.

DETAILED DESCRIPTION

Figure 1:
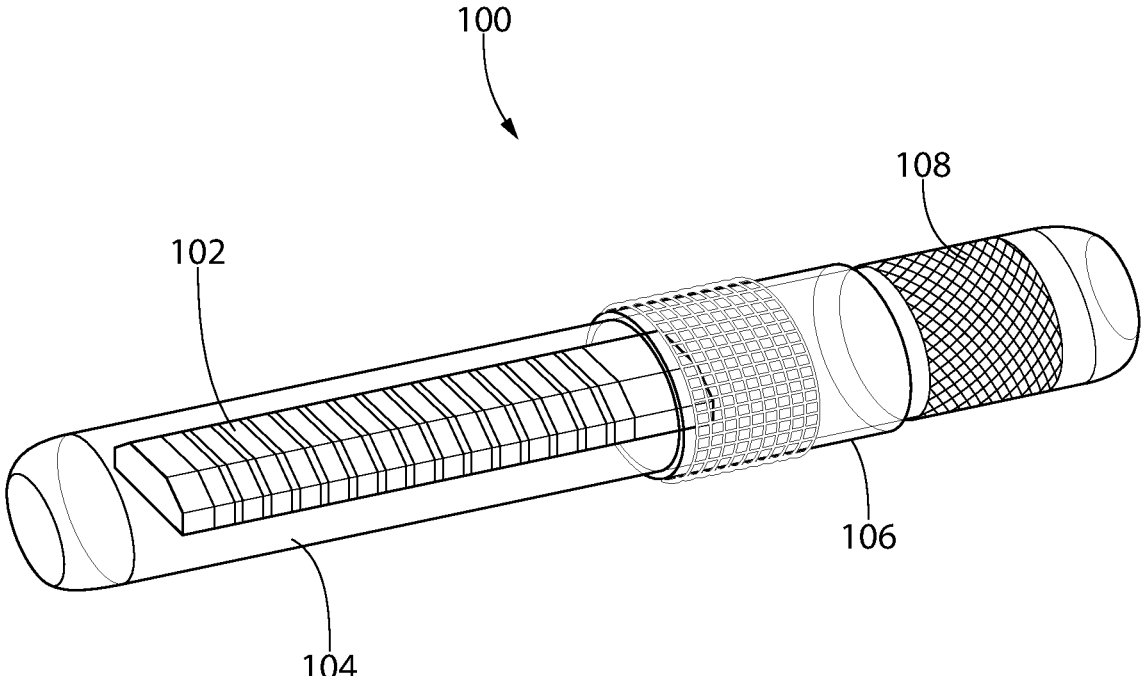
FIG. 1 shows an example implantable device that may be used to determine information relating to an animal, as described herein.

The following description of the preferred embodiment(s) is merely exemplary in nature and is in no way intended to limit the invention or inventions. The description of illustrative embodiments is intended to be read in connection with the accompanying drawings, which are to be considered part of the entire written description. In the description of the exemplary embodiments disclosed herein, any reference to direction or orientation is merely intended for convenience of description and is not intended in any way to limit the scope of the present inventions. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require a particular orientation unless explicitly indicated as such. Terms such as "attached," "affixed," "connected," "coupled," "interconnected," "secured" and other similar terms refer to a relationship wherein structures are secured or attached to one another either directly or indirectly through intervening structures, as well as both movable or rigid attachments or relationships, unless expressly described otherwise.

The discussion herein describes and illustrates some possible non-limiting combinations of features that may exist alone or in other combinations of features. Furthermore, as used herein, the term "or" is to be interpreted as a logical operator that results in true whenever one or more of its operands are true. Furthermore, as used herein, the phrase "based on" is to be interpreted as meaning "based at least in part on," and therefore is not limited to an interpretation of "based entirely on."

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Features of the present inventions may be implemented in software, hardware, firmware, or combinations thereof. The computer programs described herein are not limited to any particular embodiment, and may be implemented in an operating system, application program, foreground or background processes, driver, or any combination thereof. The computer programs may be executed on a single computer or server processor or multiple computer or server processors.

Processors described herein may be any central processing unit (CPU), microprocessor, micro-controller, computational, or programmable device or circuit configured for executing computer program instructions (e.g., code). Various processors may be embodied in computer and/or server hardware of any suitable type (e.g., desktop, laptop, notebook, tablets, cellular phones, etc.) and may include all the usual ancillary components necessary to form a functional data processing device including without limitation a bus, software and data storage such as volatile and non-volatile memory, input/output devices, graphical user interfaces (GUIs), removable data storage, and wired and/or wireless communication interface devices including Wi-Fi, Bluetooth (e.g., Bluetooth classic, Bluetooth low energy), LAN, etc.

Computer-executable instructions or programs (e.g., software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs may be referred to as a "programmable device", or "device", and multiple programmable devices in mutual communication may be referred to as a "programmable system." It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g., internal/external hard disks, floppy discs, magnetic tape CD-ROM, DVD-ROM, optical disk, ZIP™ drive, Blu-ray disk, and others), which may be written to and/or read by a processor operably connected to the medium.

In certain embodiments, examples may be embodied in the form of computer-implemented processes and apparatuses such as processor-based data processing and communication systems or computer systems for practicing those processes. The present inventions may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

Collars and other devices (e.g., harnesses, leashes) are devices used on animals, such as pets, to constrain the pet. For example, a pet may wear a collar and leash during a walk with a pet owner so that the pet remains with the pet owner. Pet collars may be used to store and/or convey information, such as identification information of the pet and/or the pet owner, address information of the pet, medical information of the pet, etc. The information may be provided via an electronic device and/or a non-electronic device. Devices (e.g., electronic devices) may be used within a collar and/or may be coupled to a collar. For example, an electronic device may be used to store information of a pet and/or a pet owner. Examples of devices that may house or couple to an electronic device may include one or more mechanisms worn by a pet for constraining the pet, storing information relating to the pet, and/or transmitting information of the pet. Such devices worn by the pet may include a harness, bracelet, anklet, belt, earring, headband, and the like.

As described herein, there may be reasons that it is desirable to use an electronic device in addition to wearing a collar, or without the wearing of a collar. For example, an electronic device (e.g., information provided by an electronic device) may be desired in addition to, or as an alternative to, a collar. As an example, information provided by an electronic device and/or to the electronic device may be desired when a pet is not wearing a collar. A pet may not wear a collar for many reasons, such as the animal's size (e.g., collars may not fit small or large animals), the collar being uncomfortable to the pet, the owner of the pet not wanting their pet to wear a collar (or wanting the pet to wear a collar for specific occasions, such as wearing GPS monitor collars for when the pet is outside), a pet owner forgetting to place a collar upon the pet, etc. In other examples, pets may not wear collars due to safety concerns around collar use, such as a danger of the collar getting caught on something, thereby presenting a choking hazard. Pets may not wear collars due to medical conditions (e.g., dermatitis, collapsed trachea, etc.), and the like. Despite the lack of a collar, there may be a continued desire to collect and/or transmit data (e.g., behavior data) relating to the pet.

Electronic devices may be positioned on locations about a pet or locations within a pet that are other than a collar of a pet. The electronic devices being positioned on locations other than a collar may be useful for pets that do not wear collars or who wear collars on a limited basis. As an example, electronic devices may be implantable within a pet. By implanting the electronic device within the pet, the electronic device may monitor and/or transfer data relating to the pet whether the pet is wearing a collar (or similar device) or not. Additional benefits of implanting the electronic device(s) may include allowing the monitoring of data (e.g., behavior data) of the pet without the need for the electronic device to be manually manipulated, for example, to complete tasks such a data transfer, power charging, and the like. Although the disclosure may use the term implant throughout, it should be understood that this is a non-limiting term. In other examples the device may be injected within the animal, coupled to the animal, as described herein.

Electronic devices may be found in one or more devices (e.g., housings) implantable within a pet. As described herein, the implantable device (e.g., housing holding one or more electronic devices) may be used in combination with one or more devices located on a collar or other article coupled to a pet. In examples, however, the implantable device may be a standalone device that is not used in combination with one or more devices located on a collar or other article coupled to a pet. As an example, the implantable device may perform services (such as monitoring data relating to the pet, storing the data relating to the pet, transferring the data relating to the pet, recharging, etc.) as a standalone device. When the implantable device acts as a standalone device it may not be used in combination with one or more devices located within a collar when monitoring behavioral data of the pet, for example.

In examples, the implantable device may communicate with one or more devices (e.g., mobile device, tablet, computer, etc.) to transfer data, provide alerts, and the like. The implantable device may communicate with one or more devices whether the implantable device is a standalone device or not a standalone device. For example, the implantable device may communicate with one or more mobile devices, tablets, computers, other implantable devices (within the same pet or within a different pet), internet of things (IoTs) devices, servers (e.g., cloud-based servers), and the like. The implantable device may communicate with one or more devices using one or more wireless communication modes known in the art, such as via Wi-Fi, Bluetooth (standard or low-e), and the like.

One or more electronic devices (e.g., electronic devices within implantable device or coupled to implantable device) may store, transmit, and/or receive information of the pet. For example, the electronic device may monitor the movement and/or location information of the pet and transmit the movement and/or location information to an external device, such as a mobile device or a server. As an example, electronic devices within implantable device may provide radio communication with a base station that may provide the location and/or proximity of the animal, Global Positioning System (GPS) devices may reside in the electronic device or communicate with the electronic device and may be used for locating the pet (e.g., over distances), etc. In examples electronic devices within implantable device may locate the pet via one or more other monitoring methods, such as via Wi-Fi location monitoring, cellular location monitoring and/or triangulation, Bluetooth tracking and/or triangulation, etc.

Electronic device(s) within implantable device may communicate with one or more mobile devices, servers, and/or base stations to provide and/or receive information. Electronic devices may communicate with devices and/or objects other than servers and base stations, as described herein. For example, electronic devices may communicate with other items, such as items found in a home. Such items may include, for example, items worn by the pet (such as pet collars), pet beds, pet feeders, litter boxes, water bowls, floors within a home in which the pet resides, implantable devices found within other pets, etc. The electronic devices may store, process, and/or communicate information relating to the pet, the owner of the pet, and/or a caregiver (e.g., veterinarian) of the pet. The electronic device and/or the objects may determine when the electronic device is proximate to the object (e.g., via a proximity sensor), and may transmit (e.g., only transmit) signals upon the electronic device and the object being proximate to one another.

Information processed by the electronic device may relate to location information of the pet, movement information of the pet, and the like, although in examples the information may be unrelated to such information. For example, the information stored, processed, and/or communicated by the electronic device may include biometric information relating to the animal. Such information may include glucose information relating to the animal, cardiac monitoring of the animal, heart rate information relating to the animal, pulse information relating to the animal, blood pressure relating to the animal, blood oxygen information relating to the animal, respiration rate information relating to the animal, temperature information relating to the animal, and the like. In other examples information relating to the animal may include address information of the animal, contact information of the animal or owner of the animal, medical information relating to the animal (such as the illnesses of the animal and/or medications taken by the animal), and the like. The information may be electronically stored, processed, and/or communicated (e.g., wirelessly communicated from the electronic device to an external device, such as a mobile device, server, and the like). As used herein, the term "information" may refer to any signals, data, or other information from a sensor or other device, as well as any signals, data, or other information derived from such information. For example, location or movement information may refer to signals or data from a sensor that are indicative of a location or movement, and may also (or alternatively) refer to data or information derived from such sensor signals or data.

FIG. 1 shows an example implantable device 100. Implantable device 100 may be implanted within an animal (e.g., subcutaneously), coupled to the animal (such as directly coupled to the body of an animal or indirectly coupled to an animal, such as being coupled to a collar worn by the animal), etc. Device 100 may be implanted (e.g., subcutaneously implanted) within an animal, for example, via an injecting of the device, via an incision, and the like. For example, device 100 may be placed under the skin of the animal via an incision, a needle, and the like. In other examples the device 100 may be placed within the body of the animal via the animal swallowing the device. In other examples the device 100 may be coupled to one more portions that may be under the skin of the animal, within the body or the animal, above the skin of the animal, outside the body of the animal, and the like.

In examples the device 100 may be implanted within an animal via a medical procedure, such as via a spay/neutering procedure of the animal. The electronic device 100 may be coupled to the animal via a suturing of the device to one or more portions of the animal, including one or more internal or external portions of the animal. In examples the device 100 may be sutured to a bone of an animal. Although the device 100 may be described as being implanted within the animal, the device may also be coupled outside of the skin of the animal, such as via a contact lens, a tooth crown, in or on the animal's hair, as an ear tag, on the tail (such as the base of the tail), on the paw, and the like. Device 100 may be implanted with a cavity of the animal, such as stomach of the animal, a scrotum of the animal. The device 100 may be implanted within a cavity of the animal created during a spay or neuter procedure of the animal (such as in the stomach or a groin of the animal, and the like).

As described herein, implantable device 100 may include one or more devices for processing, storing, transmitting, receiving, etc., information relating to the animal. For example, implantable device 100 may include one or more sensors 102. Implantable device 100 may include a housing that houses one or more electronic devices 102. Housing may be formed of one or more materials that may be tolerated within a pet when implanted. For example, the housing may be formed of one or more of polyurethane (e.g., a polyether-based thermoplastic polyurethane (TPU)), silicone, urethane acrylic, glass, ceramic, titanium, and the like.

The housing of electronic device may be formed of one material in a first portion, a second material in a second portion, etc. For example, the housing of electronic device may be formed of titanium in some titanium portions 106, and other portions (e.g., portions in which the sensors communicate) of device 100 may be formed of a polyether-based thermoplastic polyurethane. For example, FIG. 1 shows a TUP portion 104 comprised of a polyether-based thermoplastic polyurethane. The housing may be formed of one or more materials to facilitate different functions of the implantable device 100. For example, TUP portion 104 may be formed around sensors to facilitate communication of the sensors, while the titanium portions 106 may be formed around the remaining portion of device 100 (e.g., portions that do not require sensor communications).

The housing may be hermetically sealed, for example, via welding of the materials forming the housing. The device 100 (e.g., housing of implantable device 100) may be sized and/or shaped so that the pet does not experience discomfort upon the implanting of the implantable device 100 and/or while housing the implantable device 100 within or about the body of the pet. For example, the device 100 may be shaped cylindrically, as shown on FIG. 1. The implantable device 100 may be thinly shaped, and the like. In examples the implantable device 100 may be less than 10 millimeters long and 1 millimeter thick, although preferably the implantable device 100 may be less than 2 millimeters long and ½ of a millimeter thick.

One or more exterior portions of housing of implantable device 100 may be smooth, although in examples one or more portions of housing of implantable device 100 may be textured. For example, one or more portions of housing of implantable device 100 may be textured to prevent or mitigate implantable device 100 from moving within the body of the pet. In examples, housing may include (or be coupled to) one or more materials configured to prevent implantable device 100 from moving within the body of the pet. For example, housing of implantable device 100 may include a mesh portion 108 that may be configured to hold in place implantable device 100 within a portion of the body of the animal (e.g. to prevent the implantable device 100 from migrating within or about the animal).

Figure 2:
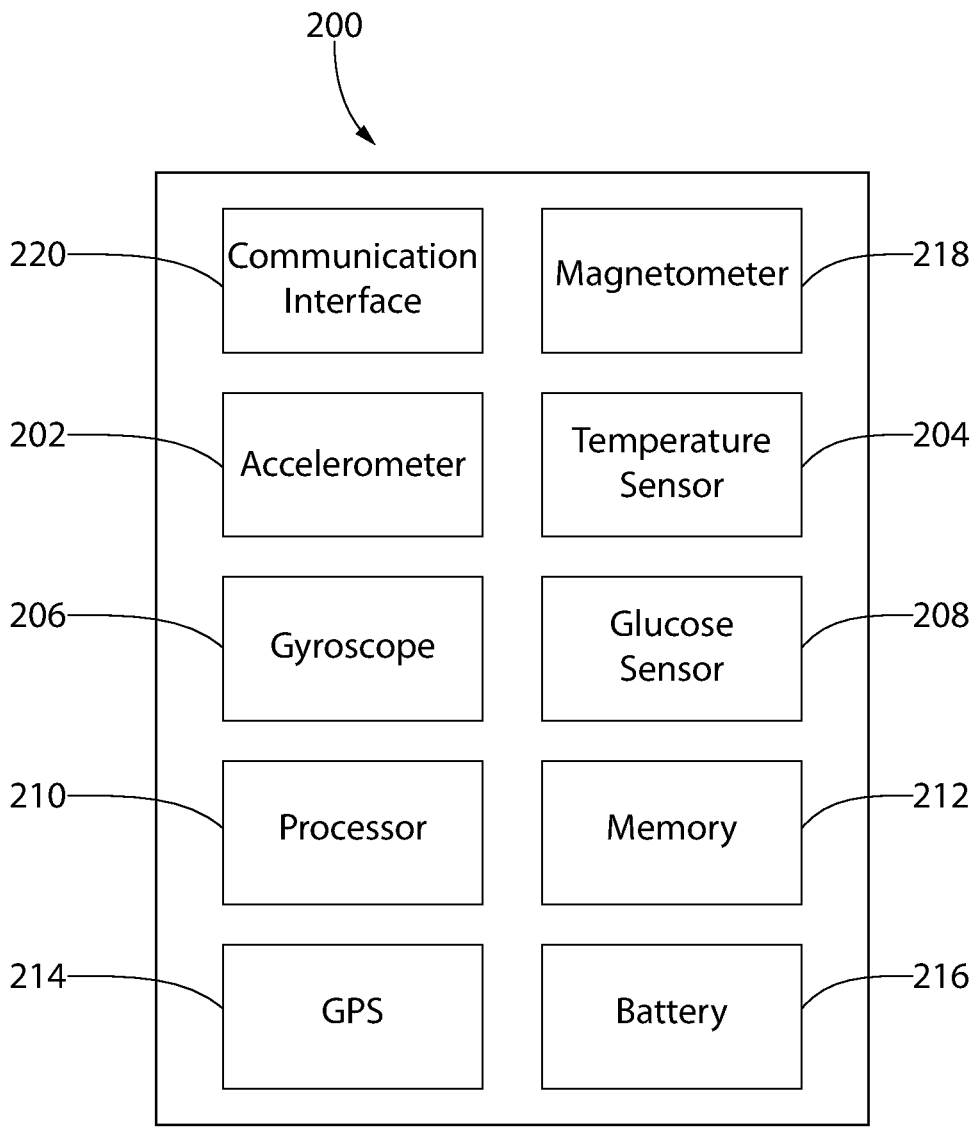
FIG. 2 shows a component diagram of an example implantable device that may be used to determine information relating to an animal, as described herein.

FIG. 2 shows an example implantable device 200 made up of one or more components. Implantable device 200 may be the same, or similar, to implantable device 100 (FIG. 1). Implantable device 200 may include one or more electronic devices. In examples, one or more of the components of implantable device 200 may be found within implantable device 200, outside of implantable device 200, or a combination thereof. One or more of the components of implantable device 200 may be used to store, process (e.g., determine), receive (e.g., actively receive, such as collect), and/or transmit information relating to the pet and/or the pet parent, including identification information, location information, medical information, biometric information, etc. The information may be real-time information and/or data that was previously processed and stored. Implantable device 200 may be one or more processors, sensors, transponders, etc., including a combination thereof.

Implantable device 200 may include and/or communicate with various components. For example, implantable device 200 may include and/or communicate with one or more of accelerometer 202, temperature sensor 204, global positioning system (GPS) sensor 214, gyroscope 206, magnetometer 218, glucose sensor 208, processor 210, memory 212, communication interface 220, and/or battery 216. One or more components (e.g., processor 210, temperature sensor 204) of the electronic device may perform additional detections, such as determining heart rate information relating to the animal, blood oxygen information relating to the animal, respiration rate information relating to the animal, temperature information relating to the animal, and the like. Implantable device 200 may communicate with one or more components that are external to the implantable device 200, via a Bluetooth connection, a Wi-Fi connection, and the like.

Processor 210 may store, receive (e.g., actively receive), and/or transmit identification information of the pet and/or pet owner. For example, processor 210 may store, receive (e.g., actively receive), and/or transmit real-time information of the pet and/or pet owner. Processor 210 may be within (e.g., integrated within) implantable device 200, although in examples one or more processors 210 may be coupled within or outside implantable device 200. Processor 210 may be configured to translate, process, and/or store data from components housed within implantable device 200 (e.g., accelerometer 202, gyroscope 206, magnetometer 218, etc.). Processor 210 may be configured to permit implantable device 200 to function and/or assist in one or more modes, such as active mode, sleep mode, transmit mode, onboarding mode, etc.

Implantable device 200 may identify and/or determine biometric data of a pet, such as a pet's glucose level, heart rate, pulse, blood pressure and/or blood oxygen level, respiration rate, temperature, etc. The biometric data may be used to determine and/or transmit a health condition of the pet, such as an unsafe temperature, glucose level, heart rate, and the like. Implantable device 200 may communicate information (e.g., biometric data, location data, movement data, etc.) to one or more persons, such as to the pet parent, a veterinarian, and the like. The implantable device 200 may communicate information via the communication interface 220 via one or more communication methodologies, such as via Bluetooth, Bluetooth Low-Energy, Wi-Fi, Cellular, and the like.

Implantable device 200 may communicate the information based on an alert (such as the animal moving beyond a designated area, the animal having an unhealthy glucose level, and the like). Implantable device 200 may determine and/or transmit location information of the pet, for example, to determine when the pet is inside/outside of the home of the pet, inside/outside a predetermined play area, and the like. Implantable device 200 may have cellular or other WAN transmission capabilities, which may provide communication capabilities with an external device, such as a mobile device, tablet, server, or the like.

Implantable device 200 may identify the pet and/or the pet owner, monitor the location of the pet, monitor biometric information of a pet or activity (e.g., heart rate, steps, calories burned, etc.) of the pet, and the like. Implantable device 200 may identify such information via one or more sensors, such as accelerometers, gyroscopes, glucose sensors, temperature sensors, heart rate sensors, magnetometers, electrocardiogram (EKG, otherwise known as ECG) electrodes, photoplethysmography (PPGs) and/or reflection mode PPGs (PPGr) sensors, or one or more other sensors of implantable device 200 or external to implantable device 200 that detect information of an animal. For example, implantable device 200 may identify biometric data of the animal via biosensors to determine health indicators of the animal, such as glucose, cortisol, serotonin, serum symmetric dimethylarginine (SDMA), and other indicators of the animal. Processor 210 may monitor such data over certain time periods. An example processor 210 may be an ARM Cortex M0-M3, or the like.

Accelerometer 202 may measure an activity and/or movement of a pet. Temperature sensor 204 may measure the pet's body temperature, gyroscope 206 may measure the pet's orientation, and/or GPS 214 may identify and/or determine the location (e.g., current location) of the pet. Memory 212 may be of any size. To perform proximity sensing, electronic device may include a cellular chip, Bluetooth (e.g., Bluetooth low energy), and the like.

Battery 216 may be contained within (e.g., self-contained within) a housing of implantable device 200 and/or may be located about (e.g., outside) housing of implantable device 200. Battery 216 may store a charge for operation of implantable device 200. Battery 216 may be chargeable (e.g., wirelessly chargeable, chargeable via a wire) while electronic device 200 is implanted within pet. For example, a wireless interface may be provided via implantable device 200 that may allow the battery 216 to be charged while implantable device 200 (e.g., implantable device 104) is within the body of the pet. Sensor (e.g., proximity sensor) may be used to determine if implantable device 200 is near a charging device. If the electronic device 200 is determined to be proximate to the charging device the charging device may charge battery 216 of device 200. For example, if the electronic device 200 is determined to be within five feet of a charging device, ten feet of a charging device, thirty feet of a charging device, etc., the charging device may charge battery 216 of device 200. Although the disclosure describes the charging device being external to the animal, in examples the charging device may be internal to the animal, such as below the skin of the anima, within the body of the animal, attached to the animal, and the like.

Implantable device 200 may receive power via one or more batteries, such as a Li—Po battery, although such battery is for illustration purposes only and any type of battery may be used. In examples, implantable device 200 may receive power from charging device at substantially the same time as the implantable device 200 receives information (e.g., location information, movement information, biometric information) from the external device, although in examples the power and information relating to the animal may be received as separate times.

The information relating to the animal may be associated with a priority. For example, the accelerometer, gyroscope, magnetometer, biometric, etc., data may be associated with a priority. The priority may determine the order in which the information is processed, received, stored, and/or received with device 200 and external devices. The information relating to the animal may be associated with a priority to preserve (e.g., reduce) power consumed and/or used by the device 200. The priority may be evaluated and/or determined based on the amount of power available to device 200. For example, device 200 may wirelessly and/or transcutaneously communicate information with an external device according to predetermined priority rules and/or the amount of power available to the device 200. As described herein, the information may include accelerometer, gyroscope, magnetometer, biometric, location, etc., data. The priority in which the data is sent may be based on predetermined settings and/or on user requests. For example, a user request may receive a higher priority than information processed by device 200 based on a periodic. The user may indicate the priority to be assigned to the user request, such as indicating that a user request is to be assigned a low priority, a high priority, and the like.

As an example, device 200 may be configured to communicate to the external device information derived from the accelerometer, the magnetometer, and the gyroscope. In an example, the information derived from the accelerometer may have (e.g., be assigned) a higher priority than the information derived from the magnetometer and gyroscope, although in other examples the magnetometer and/or gyroscope may have a higher priority than the accelerometer data. As another example, the priority of the information derived from the gyroscope may be increased during periods in which the animal is performing intense physical activity (such as when the animal is running or jumping). Biometric data may have a higher priority than one or more types of information, such as accelerometer, magnetometer, gyroscope, and location data. The priority assigned to the biometric data may be based on a safety concern. For example, biometric data relating to an unsafe temperature, heartbeat, glucose level, etc., of the animal may have a high priority level. Based on the high priority level, such information may be provided from device 200 to external device, such as to a user's mobile device, an external server, etc. In other examples data may be assigned lower priorities based on the activities of the animal, the time of day, the time of year, etc. For example, the priority of the information derived from the accelerometer and magnetometer may be lowered during light activity periods of the animal, during times at which the animal may be resting, sleeping, eating, urinating, and/or defecating.

Location data of the animal may have a higher priority than one or more types of information, such as accelerometer, magnetometer, gyroscope, and biometric data. The priority assigned to the location data may be based on a safety concern. For example, the location data may be assigned an increased priority if the animal moves into a prohibited area, such as outside of the yard of the pet parent, a water area, the street, and the like.

One or more pieces of data determined and/or stored by device may be combined and/or used with the one or more other pieces of data. For example, information derived from the magnetometer may be used with information derived from the accelerometer to estimate a distance traveled by the animal. In another example, information derived from the gyroscope may be used with information derived from the accelerometer to estimate a distance traveled by the animal. In another example, location data may be used with one or more pieces of data, such as the speed at which the animal is moving, the direction in which the animal is moving, the glucose level of the animal, etc.

Figure 3:
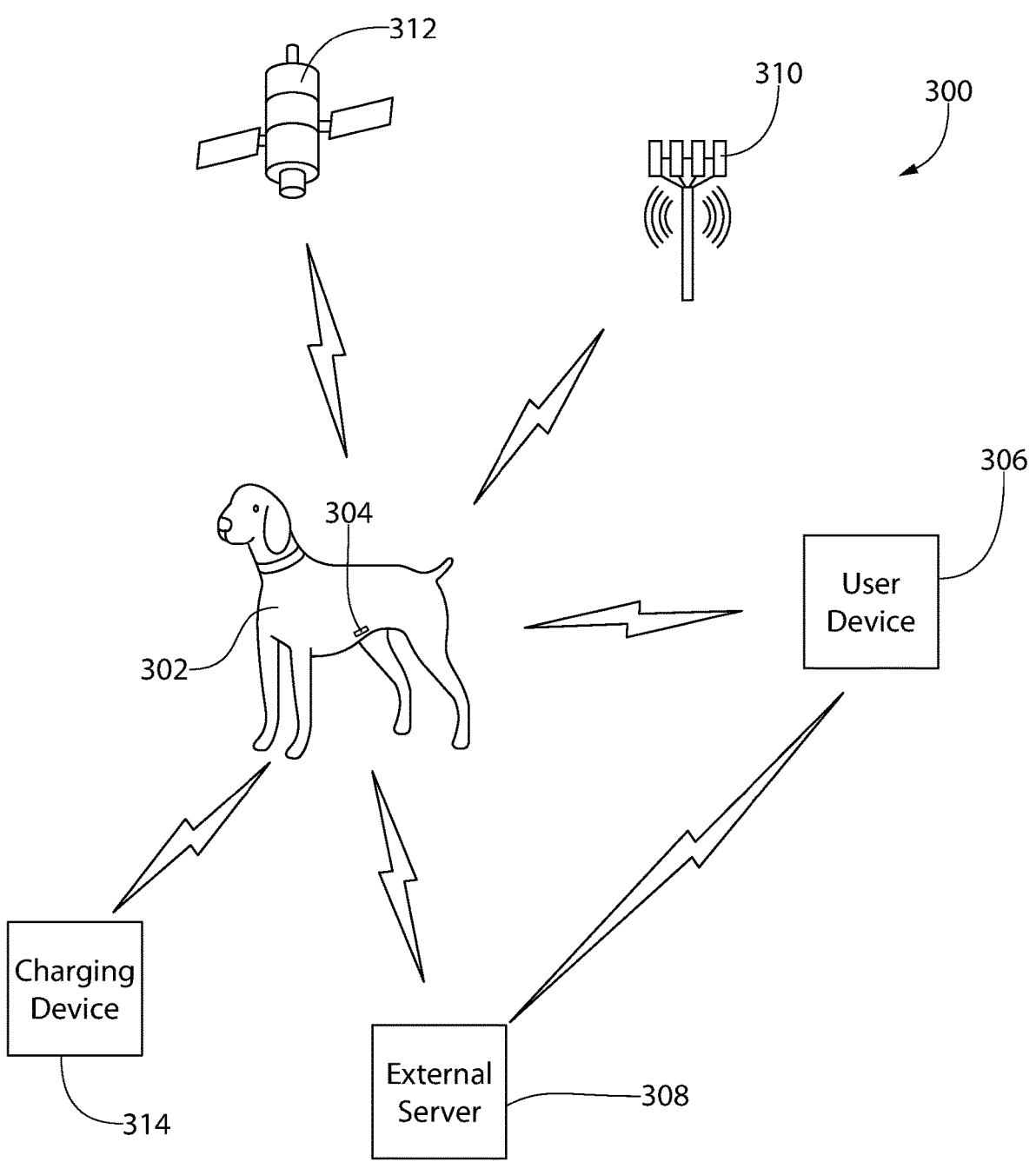
FIG. 3 is an example system in which information relating to an animal may be provided by an implantable device, as described herein.

FIG. 3 shows an example system 300 which includes a pet 302 and implantable device 304. Although an example location of implantable device 304 being at a belly of animal 302 is shown on FIG. 3, it should be understood that implantable device 304 may be located in one or more other locations of animal 304, such as within a back, leg, tail, groin, contact lens, tooth, and the like. In examples, implantable device 304 be under the skin of pet 302 and may not be accessible and/or visible from outside the body of pet 302. Implantable device 304 may include one or more electronic devices or couple to one or more electronic devices. System 300 may include a communication between implantable device 304 and one or more external devices, such as user devices 306, server 308, GPS 312, and cellular network 310.

System 300 may include a network configured to enable exchange of electronic communications between devices connected to the network. In examples the network may facilitate communications between implantable device 304 (e.g., electronic devices housed within or coupled to implantable device 304), one or more user devices 306, server 308 (e.g., an external server, such as a cloud server), as well as one or more electronic devices. The network may include, for example, one or more of the Internet, Wide Area Networks (WANs), Local Area Networks (LANs), analog or digital wired and wireless telephone networks (e.g., a public switched telephone network (PSTN), Integrated Services Digital Network (ISDN), a cellular network 310, and Digital Subscriber Line (DSL)), radio, television, cable, satellite, Bluetooth (e.g., Bluetooth classic and Bluetooth low energy), Medical Implant Communication System band, and/or one or more other delivery or tunneling mechanisms for carrying data. Implantable device 200 may include one or more antennas, such as two antennas, for communicating. In an example in which implantable device 200 includes one or more (e.g., two) antennas, one antenna may be used to communicate via one protocol (e.g., Bluetooth) and the one or more other antennas may be used to communicate via one or more other protocols (e.g., Wi-Fi).

System 300 may include multiple networks or subnetworks, each of which may include, for example, a wired or wireless data pathway. A network may include a circuit-switched network, a packet-switched data network, or any other network able to carry electronic communications (e.g., data or voice communications). For example, the network may include networks based on the Internet protocol (IP), the PSTN, packet-switched networks based on IP, or other comparable technologies. The network may include one or more networks that include wireless data channels and wireless voice channels. The network may be a wireless network, a broadband network, or a combination of networks including a wireless network and a broadband network.

One or more components (shown on FIG. 2) may be housed within implantable device 304, as described herein. In other examples one or more components may be housed outside of implantable device 304 and/or operationally coupled to implantable device 304. For example, one or more components of implantable device 200 may be housed within a collar, bedding, feeding bowl, waste area, as described further herein.

System 300 may include a charging device, such as charging device 314. Charging device 314 may be configured to charge one or more batteries (such as battery 216) within implantable device 302. The charging device 314 may charge the battery via one or more wired or wireless techniques. Example wireless techniques in which the charging device 314 may charge the battery may include inductive coupling, magnetic resonance coupling, microwave/RF ultrasonic (e.g., triboelectric piezoelectric), and the like.

Charging device 314 may be positioned such that implantable device 304 (e.g., animal housing implantable device 304) may be in proximity of charging device 314 or move within a proximity of charging device 314. For example, charging device 314 may be positioned near an area or a device that an animal may frequent. Examples may include charging device 314 taking one or more form factors, such as a bed of the animal, a collar of the animal, a feeding bowl of the animal, a waste area/device of the animal, a play area of the animal, floors within a room that the animal may frequent, tools used with an animal (such as a grooming tool), a pet scale, and the like. By placing the charging device 314 in one or more locations in which the animal may frequent, the charging device 314 may charge/recharge the battery (such as battery 216) of the implantable device 304 in a manner which would be unnoticed by the animal 304, would be convenient for the animal or the pet owner, and/or would not cause the animal 304 to change its habits or routines.

Figure 4:
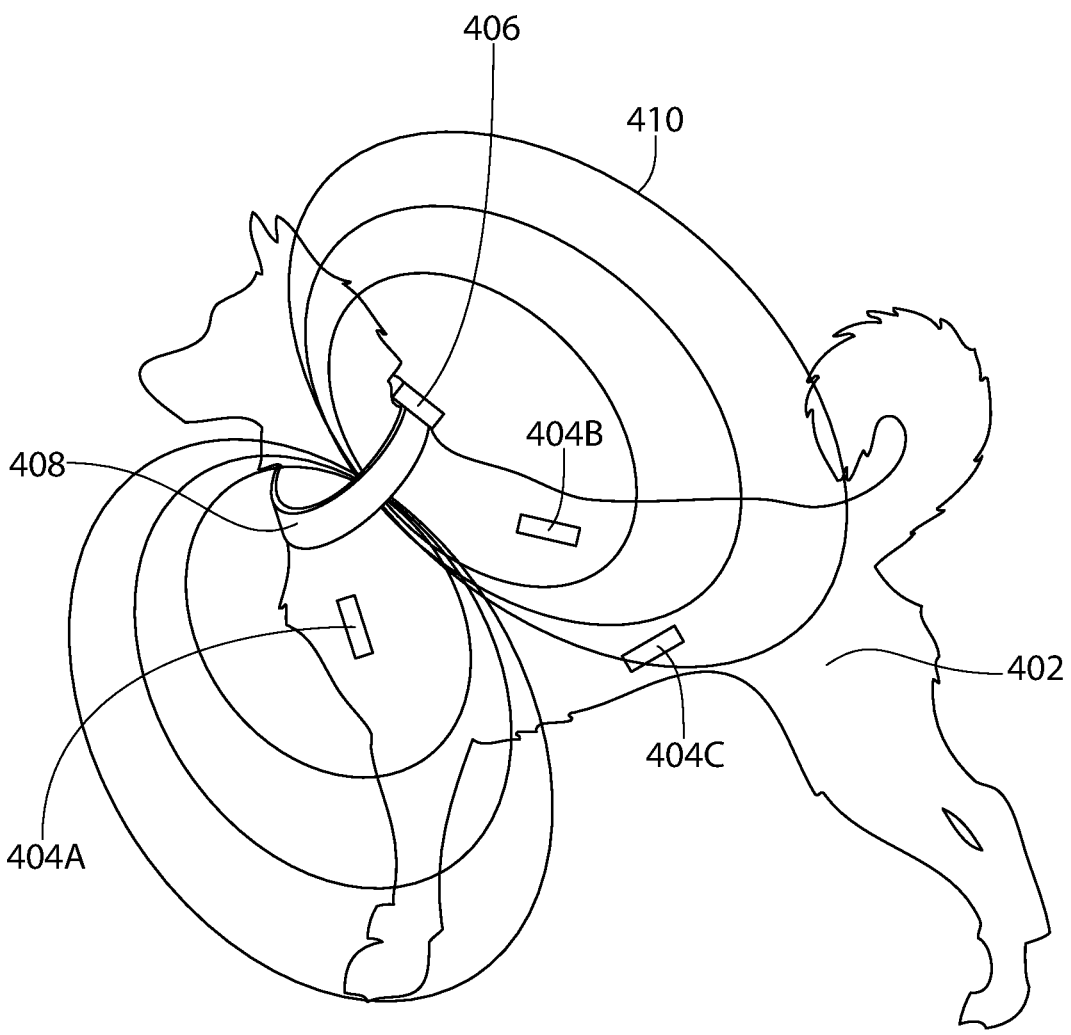
FIG. 4 is an example in which an implantable device may be charged by an external device, as described herein.

FIG. 4 shows an example in which an animal 402 is fitted with one or more implantable devices 404A, 404B, 404C (collectively implantable device 404). The implantable device may be placed in more than one location (e.g., for sensing purposes). For example, an implantable device 404 may be placed in an location (such as a chest) of the animal to determine location of the animal 402, an implantable device 404 may be placed in an location (such as an appendage) of the animal to determine an injury to the appendage or a speed of an appendage, an implantable device 404 may be placed near an organ (such as the heart) of the animal to determine the heartbeat of the animal 402, etc.

As described herein, a charging device may be positioned around or about a location in which the animal may be located (e.g., naturally located). FIG. 4 shows an example in which the charging device 406 is located on a device (e.g., collar 408) coupled to the animal. Although FIG. 4 shows an example in which the charging device 406 is located on a device (e.g., collar 408) coupled to the animal 402, such example is for illustration purposes only. In other examples the charging device 406 may be located on one or more portions of the animal 402, such as an anklet, tag (e.g., tail tag, eartag), ring (e.g., tail ring, earring), belt, and the like. In other examples, the charging device 406 may be located on one or more locations that the animal may frequent, such as a bedding of the animal, a feeding area, a waste area, and the like. In examples an external device for communicating (e.g., sending location, movement, biometric information, and the like) with the implantable device 404 may be located on the animal 402, such as on a collar 408 of the animal 402. The charging device 406 may send/receive signals 410 to and/or from one or more of the implantable devices 404. The charging device 406 may be charged via one or more techniques. For example, the charging device 406 may be charged via AC power, DC power, solar power, kinetic energy, and the like. The charging device may include an indicator indicating the amount of charge left on the charging device 406, etc.

Figure 5:
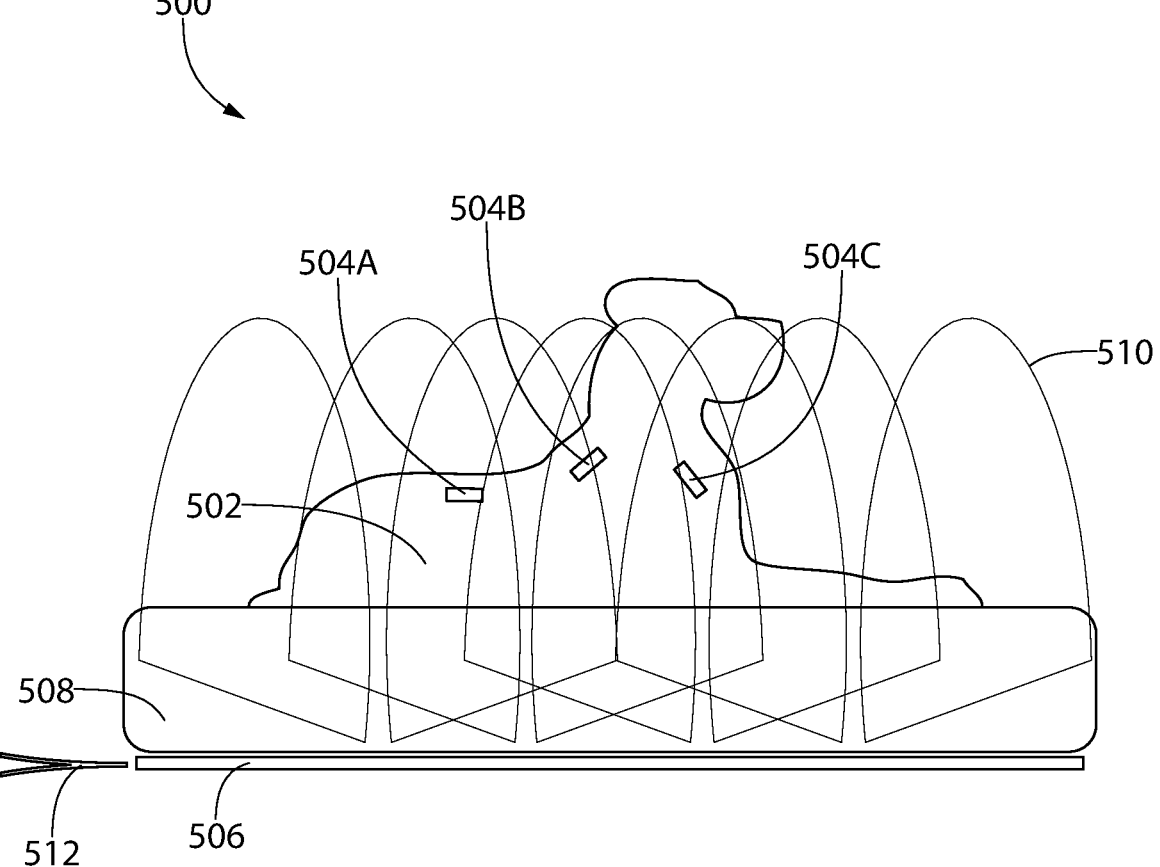
FIG. 5 is another example in which an implantable device may be charged by an external device, as described herein.

FIG. 5 is an example in which charging device 506 is placed within a location that the animal 502 may visit, such as within a bedding 508 of animal 502. Although FIG. 5 shows an example in which the charging device 506 is located within a bedding 508 of animal 502, such example is for illustration purposes only. In other examples as described herein, the charging device 506 may be located within or on a feeding device, waste device, play device, and the like. Charging device 506 may be located on one or more of a bottom, top, side, middle, etc., of bedding 508. Charging device 506 may charge one or more implantable devices 504A, 504B, 504C (collectively implantable device 504) coupled to the animal or implanted within the animal. For example, charging device 506 may send and/or receive wireless signals 510 to and/or from implantable device 504 within animal 502. The charging device 506 may be charged via one or more techniques. For example, the charging device 506 may be charged via an AC power cord 512, as shown on FIG. 5.

Figure 6:
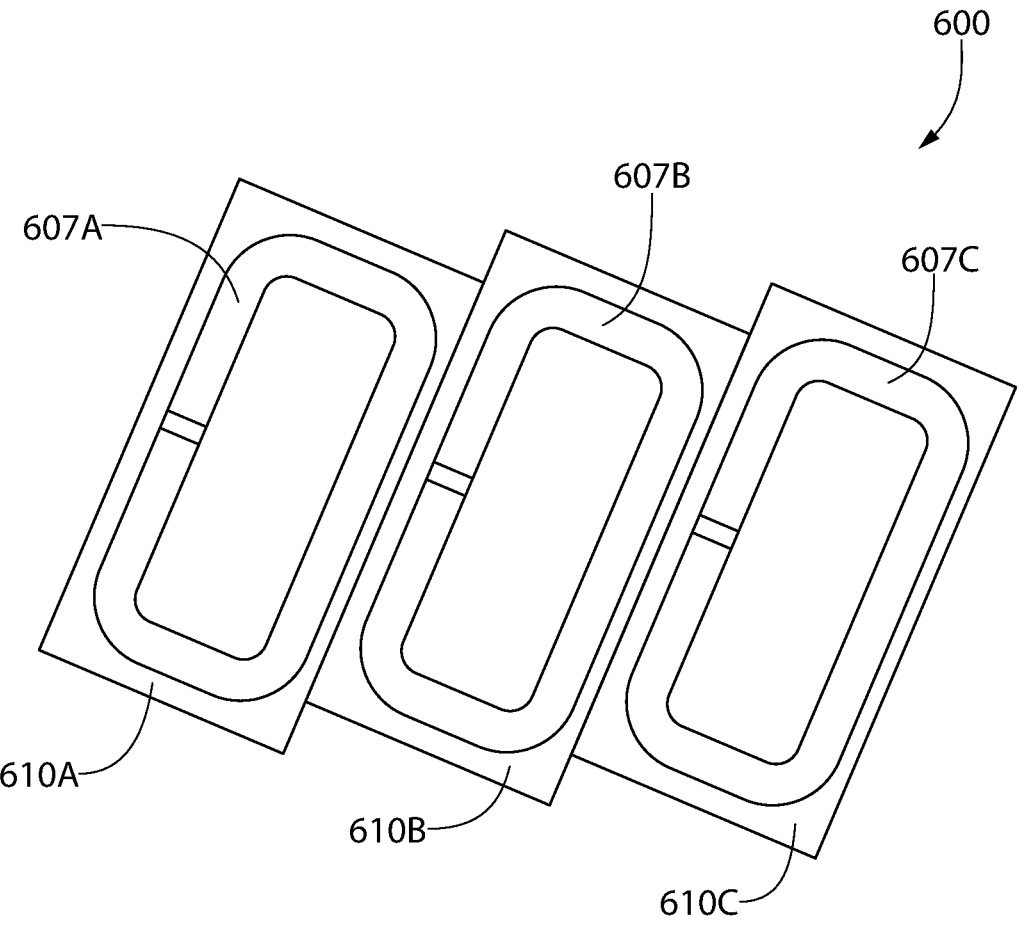
FIG. 6 is an example of a device that may be used to charge an implantable device, as described herein.

FIG. 6 shows coils 607A, 607B, 607C (collectively coils 607) that may be used to charge the implantable device, as described herein. For example, one or more coils may be located in the bedding of animal, such as bedding 508 (FIG. 5). The efficiency of the coils 607 may be based on the diameter and/or cross-section of the coils 607. A bed (e.g., small) bed may allow for a large format coil 607 that may be used for charging implantable devices. The coils 607 may be placed under, within, on the side(s) of, and/or above one or more of animal beds, animal feeders, animal waste areas, animal play areas, and the like. In an example the charging device may detect an implantable device (e.g., via a proximity sensor, a pressure sensor, a sound, an image). The charging device may provide power to the implantable device upon (e.g., only upon) detecting the implantable device. For example, a charging device may be located within a bedding. The charging device within the bedding may include a pressure sensor that detects when an animal rests upon the bedding. Upon detecting the animal resting upon the bedding the charging device may send (e.g., wirelessly send) charging signals to the implantable device. The charging device may cease sending the charging signals upon receiving an indication that the implantable device is fully charged and/or upon the charging device receiving an indication that the animal is no longer resting upon the bedding (e.g., the pressure sensor within the bedding may detect that the pressure upon the bedding has ceased).

In other examples, a charging device may include a camera or microphone that may detect the presence or absence of the animal. For example, a feeding bowl may include a microphone that detects the presence (via sound) of an animal. The charging device may provide a power signal when the charging device detects the animal proximate the feeding bowl and may cease power signals upon the animal leaving the proximity of the feeding bowl. Another example may include a play area including a charging device having a camera (e.g., still or moving camera) that detects the presence of the animal or absence of the animal. The charging device may send charging signals upon the charging device detecting the animal proximate the play area and may cease power signals upon the animal leaving the proximity of the play area. The charging device may perform one or more additional functions in addition to providing power to the implantable device. For example, the charging device may be configured to receive and/or send information relating to the animal, such as location data, movement data, biometric data, and the like. The charging device may be configured to save information relating to the animal, process information relating to the animal, and the like.

FIG. 7 shows an example process 700 for using an implantable device (e.g., an electronic device, such as device 100, 200) configured to provide information relating to an animal. At 702, the electronic device may be implanted within the animal and/or coupled to the animal, as described herein. For example, the implantable device may be implanted under the skin of the animal, within the body of the animal, attached to the animal via a contact lens, earring, and the like. The electronic device may include one or more components, such as one or more sensors, memories, communication interfaces, batteries, etc.

At 704, the sensors of the electronic device may determine information relating to the animal. The information may relate to location and/or movement information of the animal, biometric information relating to the animal, etc. At 706 the information may be stored. The information may be stored on the electronic device and/or one or more external devices, such as a mobile device or server. At 708 the information may be communicated (e.g., wirelessly communicated) to one or more devices, such as a mobile device or external server. The information may be communicated via one or more technologies, such as via Wi-Fi, Bluetooth (e.g., Bluetooth classic, Bluetooth low energy), LAN, etc.

At 710 power may be provided to the electronic device. For example, one or more batteries of the electronic device may be charged (e.g., recharged). The one or more batteries of electronic device may be charged while the electronic device is implanted within the animal, in examples, although in other examples the batteries of the electronic device may be charged while the electronic device is removed from the animal. Batteries of the electronic device may be wirelessly chargeable, chargeable via a wire. For example, a wireless interface may be provided via electronic device that may allow the batteries to be charged while the electronic device is within the body of the pet.

In examples a sensor (e.g., proximity sensor) may be used to determine if the electronic device is near a charging device, as described herein. If the electronic device is determined to be proximate to the charging device (e.g., only if the electronic device is determined to be proximate to the charging device), the charging device may charge the battery. For example, if the electronic device is determined to be within five feet of the charging device, ten feet of the charging device, thirty feet of charging device, etc., the charging device may charge battery of the electronic device. The electronic device may receive power via one or more batteries, such as a Li—Po battery, although such battery is for illustration purposes only and any type of battery may be used.

While the inventions have been described with respect to specific examples including presently preferred modes of carrying out the inventions, those skilled in the art will appreciate that there are numerous variations and permutations of the above described systems and techniques. It is to be understood that other embodiments may be utilized and structural and functional modifications may be made without departing from the scope of the present inventions. Thus, the spirit and scope of the inventions should be construed broadly as set forth in the appended claims.

What is claimed is:

1. A system for tracking an animal comprising:
an electronic device configured to be coupled to an animal, the electronic device comprising:
(a) one or more sensors comprising at least one of an accelerometer, a gyroscope, or a magnetometer, the one or more sensors configured to determine location or movement information relating to the animal;

(b) a memory device configured to store the location or movement information relating to the animal;

(c) a communication interface configured to wirelessly communicate the location or movement information to an external device; and (d) a battery device for providing power to the at least one of the one or more sensors or the communication interface;

a charging device configured to detect a presence of the electronic device or the animal, and to provide power to the electronic device upon detecting the presence of the electronic device or the animal; and wherein the electronic device and the charging device are configured to be implanted within the animal.

2. The system of claim 1, wherein the electronic device is housed within at least one of a contact lens, an earring, a tag, or a tooth crown for the animal.

3. The system of claim 1, wherein the communication interface receives the location or movement information from the external device at substantially the same time as the battery receives power from charging device.

4. The system of claim 1, wherein the electronic device is configured to be implanted within the animal and the charging device is configured to be located outside the animal.

5. The system of claim 1, wherein the charging device provides power to the battery device via Bluetooth.

6. The system of claim 1, wherein the charging device is positioned within at least one of a food dish of the animal, a bedding of the animal, a waste area of the animal, or a grooming tool of the animal.

7. The system of claim 1, wherein the charging device is positioned about a collar worn by the animal.

8. The system of claim 1, wherein the charging device provides power to the battery device via at least one of inductive coupling, magnetic resonance coupling, or microwave/RF ultrasonic techniques.

9. A method for tracking an animal comprising:

coupling an electronic device to an animal, the electronic device comprising:

(a) one or more sensors comprising at least one of an accelerometer, a gyroscope, or a magnetometer;

(b) a memory device operably coupled to the one or more sensors;

(c) a communication interface operably coupled to the memory device or the one or more sensors; and (d) a battery device for providing power to at least one of the one or more sensors or the communication interface;

detecting, by a charging device, a presence of at least one of: the electronic device, or the animal;

providing power, via the charging device, to the electronic device upon the detecting the presence of the at least one of: the electronic device, or the animal;

determining, using the one or more sensors, location or movement information relating to the animal;

storing, by the memory device, the location or movement information; wirelessly communicating, by the communication interface, the location or movement information to an external device; and wherein the electronic device and the charging device are implanted within the animal.

10. The method of claim 9, wherein the electronic device is housed within at least one of a contact lens, an earring, a tag, or a tooth crown for the animal.

11. The method of claim 9, wherein the communication interface receives the location or movement information from the external device at substantially the same time as the battery receives power from charging device.

12. The method of claim 9, wherein the electronic device is implanted within the animal and the charging device is located outside the animal.

13. The method of claim 9, wherein the charging device provides power to the battery device via Bluetooth.

14. The method of claim 9, wherein the charging device is positioned within at least one of a food dish of the animal, a bedding of the animal, a waste area of the animal, or a grooming tool of the animal.

15. The method of claim 9, wherein the charging device is positioned about a collar worn by the animal.

16. The method of claim 9, wherein the charging device provides power to the battery device via at least one of inductive coupling, magnetic resonance coupling, or microwave/RF ultrasonic techniques.

\* \* \* \* \*